United States Patent
Thomas et al.

(10) Patent No.: US 12,391,637 B2
(45) Date of Patent: Aug. 19, 2025

(54) METHODS TO SEPARATE CANNABINOIDS FROM IMPURITIES BY CRYSTALLIZATION

(71) Applicant: Natural Extraction Systems, LLC, Boulder, CO (US)

(72) Inventors: C. Russell Thomas, Boulder, CO (US); Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 753 days.

(21) Appl. No.: 17/775,856

(22) PCT Filed: Nov. 10, 2020

(86) PCT No.: PCT/US2020/059884
§ 371 (c)(1),
(2) Date: May 10, 2022

(87) PCT Pub. No.: WO2021/096886
PCT Pub. Date: May 20, 2021

(65) Prior Publication Data
US 2022/0396540 A1    Dec. 15, 2022

Related U.S. Application Data

(60) Provisional application No. 63/056,311, filed on Jul. 24, 2020, provisional application No. 62/933,751, filed on Nov. 11, 2019.

(51) Int. Cl.
*C07C 37/84*    (2006.01)

(52) U.S. Cl.
CPC .......... *C07C 37/84* (2013.01); *C07B 2200/13* (2013.01)

(58) Field of Classification Search
CPC ........................... C07C 37/84; C07B 2200/13
See application file for complete search history.

(56) References Cited

U.S. PATENT DOCUMENTS

| 10,189,762 B1 * | 1/2019 | Oroskar ................. C07C 37/82 |
| 10,610,805 B1 | 4/2020 | Metcalf |
| 11,021,674 B2 | 6/2021 | Thomas |
| 2004/0138293 A1 | 7/2004 | Werner et al. |
| 2007/0072939 A1 | 3/2007 | Kupper |

OTHER PUBLICATIONS

International Search Report and Written Opinion issued by the International Searching Authority in PCT/U2020/059884 mailed Feb. 18, 2021, 9 pages.

* cited by examiner

*Primary Examiner* — Sikarl A Witherspoon
(74) *Attorney, Agent, or Firm* — Douglas G. Metcalf

(57) ABSTRACT

Various aspects of this patent document relate to compositions and methods to purify cannabinoids by crystallization in a water-miscible liquid.

20 Claims, No Drawings

METHODS TO SEPARATE CANNABINOIDS FROM IMPURITIES BY CRYSTALLIZATION

CROSS-REFERENCE TO RELATED APPLICATIONS

This patent application claims priority to U.S. Provisional Patent Application No. 62/933,751, filed Nov. 11, 2019, and U.S. Provisional Patent Application No. 63/056,311, filed Jul. 24, 2020, each of which is incorporated by reference in its entirety.

BACKGROUND

Cannabidiol, which is the active ingredient in the pharmaceutical EPIDIOLEX®, is isolated from impurities by crystallization in pentane, for example, because pentane can dissolve impurities such as the psychoactive drug tetrahydrocannabinol. Pentane presents safety risks, for example, because pentane/air mixtures can detonate. Pentane also generally lacks compatibility with USDA organic certification. Methods are desirable to isolate cannabidiol and other cannabinoids including cannabidivarin, cannabigerol, and cannabigerovarin without relying upon hydrocarbon solvents.

SUMMARY

Various aspects of this patent document relate to compositions and methods to purify cannabinoids by crystallization in a water-miscible liquid.

DETAILED DESCRIPTION

Various aspects of this patent document relate to a method to produce cannabinoid crystals.

In some embodiments, the method comprises providing a precursor composition that comprises (i) a precursor, (ii) contaminant precursors, (iii) original lipids, and (iv) original organic matter, wherein: either (i) the precursor is cannabidiolic acid, and the contaminant precursors consist of tetrahydrocannabinolic acid and cannabichromenic acid, or (ii) the precursor is cannabidivarnic acid, and the contaminant precursors consist of tetrahydrocannabivarin acid and cannabichromevarin acid; the original lipids consist of one or more of n-nonane; n-decane; n-undecane; n-dodecane; n-tridecane; n-tetradecane; n-pentadecane; n-hexadecane; n-heptadecane; n-octadecane; n-nonadecane; n-icosane; n-heneicosane; n-docosane; n-tricosane; n-tetracosane; n-pentacosane; n-hexacosane; n-heptacosane; n-octacosane; n-nonacosane; n-triacontane; n-hentriacontane; n-dotriacontane; 3,6-dimethyl-tridecane; 2,6-dimethyl-tetradecane; 2,6-dimethyl-hexadecane; 3,6-dimethyl-heptadecane; 3,7-dimethyl-heptadecane; 3,6-dimethyl-octadecane; 3,7-dimethyl-octadecane; 3-methyl-heneicosane; 3-methyl-tricosane; 2-methyl-tetracosane; 3-methyl-pentacosane; 2-methyl-hexacosane; 3-methyl-heptacosane; and 3-methyl-triacontane; the original organic matter consists of plant-derived molecules and ions that do not vaporize at any temperature of less than 235 degrees Celsius at atmospheric pressure; and the precursor composition comprises the precursor at a concentration of at least 4 percent by mass.

In some embodiments, the method comprises heating the precursor composition to produce a decarboxylated composition that comprises (i) a cannabinoid, (ii) contaminants, (iii) lipids, and (iv) organic matter, wherein: the heating converts at least 90 percent of the precursor into (i) the cannabinoid and (ii) carbon dioxide by mole of the precursor; either (i) the precursor is cannabidiolic acid, and the cannabinoid is cannabidiol, or (ii) the precursor is cannabidivarnic acid, and the cannabinoid is cannabidivarin; the heating converts at least 90 percent of the contaminant precursors into (i) the contaminants and (ii) carbon dioxide by mole of the contaminant precursors; either (i) the contaminant precursors consist of tetrahydrocannabinolic acid and cannabichromenic acid, and the contaminants consist of tetrahydrocannabinol and cannabichromene, or (ii) the contaminant precursors consist of tetrahydrocannabivarin acid and cannabichromevarin acid, and the contaminants consist of tetrahydrocannabivarin and cannabichromevarin; the lipids consist of a portion of the original lipids that survive the heating; and the organic matter consists of a portion of the original organic matter that survives the heating.

In some embodiments, the method comprises combining a portion of the decarboxylated composition with ethanol to produce a dewaxing composition that comprises (i) ethanol, (ii) a portion of the cannabinoid of the decarboxylated composition, (iii) a portion of the contaminants of the decarboxylated composition, (iv) a portion of the lipids of the decarboxylated composition, and (v) a portion of the organic matter of the decarboxylated composition, wherein: the portion of the cannabinoid of the decarboxylated composition comprises the cannabinoid at a concentration of at least 30 percent and no greater than 80 percent by mass; the portion of the cannabinoid of the decarboxylated composition comprises the cannabinoid and the contaminants at a ratio of at least 3:1 and no greater than 80:1 by mass; the portion of the cannabinoid of the decarboxylated composition comprises the cannabinoid and the lipids at a concentration of at least 1:2 and no greater than 40:1 by mass; the portion of the cannabinoid of the decarboxylated composition comprises the cannabinoid and the organic matter at a concentration of at least 1:2 and no greater than 40:1 by mass; and the dewaxing composition comprises the ethanol at a concentration of at least 20 percent and no greater than 90 percent by mass.

In some embodiments, the method comprises cooling a portion of the dewaxing composition to produce a mixture that comprises (i) a portion of the ethanol of the dewaxing composition, (ii) a portion of the cannabinoid of the dewaxing composition, (iii) a portion of the contaminants of the dewaxing composition, (iv) a portion of the lipids of the dewaxing composition, and (v) a portion of the organic matter of the dewaxing composition, wherein: the mixture comprises a solid phase and a liquid phase; the cooling converts at least 65 percent of the portion of the lipids of the dewaxing composition into solid-phase lipids by mass such that the solid phase of the mixture comprises at least 65 percent of the lipids of the mixture by mass; the liquid phase comprises at least 90 percent of the ethanol of the mixture by mass; the liquid phase comprises at least 90 percent of the cannabinoid of the mixture by mass; the liquid phase comprises at least 90 percent of the contaminants of the mixture by mass; and the liquid phase comprises at least a portion of the organic matter of the mixture.

In some embodiments, the method comprises separating a portion of the liquid phase from the solid phase to produce a dewaxed composition that comprises (i) a portion of the ethanol of the liquid phase, (ii) a portion of the cannabinoid of the liquid phase, (iii) a portion of the contaminants of the liquid phase, and (iv) a portion of the organic matter of the liquid phase.

In some embodiments, the method comprises separating ethanol from a portion of the dewaxed composition to produce a concentrate composition that comprises (i) a portion of the cannabinoid of the dewaxed composition, (ii) a portion of the contaminants of the dewaxed composition, and (iii) a portion of the organic matter of the dewaxed composition, wherein: the separating is performed by vaporizing the ethanol from the portion of the dewaxed composition; and the concentrate composition lacks ethanol at a concentration greater than 20 percent by mass.

In some embodiments, the method comprises heating a portion of the concentrate composition to produce a vapor phase and residual organic matter, wherein: the portion of the concentrate composition comprises the cannabinoid and the contaminants at a combined concentration of at least 40 percent and no greater than 85 percent by mass; the vapor phase comprises (i) a portion of the cannabinoid of the concentrate composition and (ii) a portion of the contaminants of the concentrate composition; the residual organic matter comprises a portion of the organic matter of the concentrate composition; and the residual organic matter consists of one or both of a solid and a liquid.

In some embodiments, the method comprises separating a portion of the vapor phase from the residual organic matter to produce a distillate that comprises (i) a portion of the cannabinoid of the vapor phase and (ii) a portion of the contaminants of the vapor phase.

In some embodiments, the method comprises condensing a portion of the distillate into a condensed phase that comprises (i) a portion of the cannabinoid of the distillate, and (ii) a portion of the contaminants of the distillate, wherein: the condensed phase comprises the cannabinoid at a concentration of at least 70 percent and no greater than 90 percent by mass; and the condensed phase comprises the contaminants at a concentration of at least 1 percent and no greater than 20 percent by mass.

In some embodiments, the method comprises combining a portion of the condensed composition and ethanol to produce a crystallization composition that comprises (i) ethanol, (ii) a portion of the cannabinoid of the condensed phase, and (iii) a portion of the contaminants of the condensed phase.

In some embodiments, the method comprises incubating a portion of the crystallization composition at a crystallization temperature to produce crystals and residual liquid, wherein: the cannabinoid has both a concentration and a solubility in the portion of the crystallization composition, and the crystallization temperature is a temperature at which the concentration is greater than the solubility; the crystals comprise a portion of the cannabinoid of the crystallization composition; and the residual liquid comprises a portion of the ethanol of the crystallization composition and a portion of the contaminants of the crystallization composition.

In some embodiments, the method comprises separating a portion of the crystals from the residual liquid to produce a product, wherein: the product comprises the cannabinoid at a concentration of at least 90 percent by mass; the product lacks the contaminants at a concentration of greater than 0.3 percent by mass; the product lacks the lipids at a concentration of greater than 1 percent by mass; the product lacks the organic matter at a concentration greater than 1 percent by mass; the crystals are a solid; the crystals have a melting point; and the crystals lack a glass-transition temperature. In some specific embodiments, the crystallization composition comprises water.

"Comprising" and "comprise(s)" refer to open sets such that a composition that comprises ethanol, for example, can also comprise water.

"Consist(s) of" refers to closed sets such that a composition that consists of ethanol, for example, cannot also comprise water.

"Consist(s) essentially of" refers to a closed set that optionally comprises one or more unidentified elements either at (i) a trace amount; (ii) an amount that cannot be eliminated in a commercially viable process; or (iii) an amount that does not interfere with the ordinary practice of a composition or method described in this patent application, which includes amounts added in an attempt to circumvent the claims set forth in this document.

"Cannabidiolic acid" refers to 2,4-dihydroxy-3-[(1R,6R)-6-isopropenyl-3-methylcyclohex-2-en-1-yl]-6-pentylbenzene-1-carboxylic acid.

"Tetrahydrocannabinolic acid" refers to (6aR,10aR)-1-hydroxy-6,6,9-trimethyl-3-pentyl-6a,7,8,10a-tetrahydro-6H-benzo[c]chromen-2-carboxylic acid.

"Cannabichromenic acid" refers to 2-methyl-2-(4-methylpent-3-en-1-yl)-5-hydroxy-7-pentyl-2H-1-benzopyran-6-carboxylic acid without regard to stereochemistry.

"Cannabidivarinic acid" refers to 2,4-dihydroxy-3-[(1R,6R)-6-isopropenyl-3-methylcyclohex-2-en-1-yl]-6-propyl-benzene-1-carboxylic acid.

"Tetrahydrocannabivarin acid" refers to (6aR,10aR)-1-hydroxy-6,6,9-trimethyl-3-propyl-6a,7,8,10a-tetrahydro-6H-benzo[c]chromen-2-carboxylic acid.

"Cannabichromevarin acid" refers to 2-methyl-2-(4-methylpent-3-en-1-yl)-5-hydroxy-7-propyl-2H-1-benzopyran-6-carboxylic acid without regard to stereochemistry.

"Cannabidiol" refers to 2-[(1R,6R)-6-isopropenyl-3-methylcyclohex-2-en-1-yl]-5-pentylbenzene-1,3-diol.

"Tetrahydrocannabinol" refers to (6aR,10aR)-6,6,9-trimethyl-3-pentyl-6a,7,8,10a-tetrahydro-6H-benzo[c]chromen-1-ol.

"Cannabichromene" refers to 2-methyl-2-(4-methylpent-3-en-1-yl)-5-hydroxy-7-pentyl-2H-1-benzopyran without regard to stereochemistry.

"Cannabidivarin" refers to 2-[(1R,6R)-6-isopropenyl-3-methylcyclohex-2-en-1-yl]-5-propylbenzene-1,3-diol.

"Tetrahydrocannabivarin" refers to (6aR,10aR)-6,6,9-trimethyl-3-propyl-6a,7,8,10a-tetrahydro-6H-benzo[c]chromen-1-ol.

"Cannabichromevarin" refers to 2-methyl-2-(4-methylpent-3-en-1-yl)-5-hydroxy-7-propyl-2H-1-benzopyran without regard to stereochemistry.

Various aspects of this patent document relate to a composition, comprising a cannabinoid, an impurity, a liquid phase, and a solid phase, wherein: the cannabinoid has the molecular formula $C_xH_yO_2$; the impurity has the molecular formula $C_xH_zO_2$; "x" is at least 17 and no greater than 24; "y" is at least 22 and no greater than 36; "z" is at least 22 and no greater than 34; the cannabinoid and the impurity each comprise an alkyl; the alkyl of the cannabinoid is identical to the alkyl of the impurity; the alkyl is either methyl, propyl, pentyl, hexyl, or heptyl; the cannabinoid is either (i) 2-[(1R,6R)-6-isopropenyl-3-methylcyclohex-2-en-1-yl]-5-alkylbenzene-1,3-diol, and "z" equals "y" minus either 0, 2, or 4, or (ii) 2-[(2E)-3,7-dimethylocta-2,6-diene-1-yl]-5-alkylbenzene-1,3-diol, and "z" equals "y" minus either 2, 4, or 6; the impurity comprises a 2H-chromene ring that either (i) comprises exactly 4 substituents that consist of a 2-methyl substituent; a 2-(4-methylpent-3-en-1-yl) substituent; a 5-hydroxy substituent; and a 7-alkyl substituent that is the alkyl of the impurity, wherein "z" equals "y" minus either 0 or 2 or (ii) is the 2H-chromene of a 6H-benzo[c]chromene ring that comprises exactly 5 substituents that consist of a 1-hydroxy substituent; a 3-alkyl substituent that is the alkyl of the impurity; two 6-methyl substituents; and a 9-methyl substituent, wherein "z" equals "y" minus either 0, 2, 4, or 6; the composition comprises the cannabinoid and the impurity at a ratio of at least 3:1 and no greater than 333:1 by mass; the liquid phase consists of one or more liquids; the liquid phase has an average density of at least 770 and no greater than 1260 grams per liter; the liquid phase comprises greater than 50 percent of the impurity of the composition by mass; the liquid phase is in both physical and chemical communication with the solid phase such that the physical and chemical properties of the composition control the extent to which the cannabinoid partitions between the liquid phase and the solid phase; the solid phase consists of one or more solids; the solid phase comprises greater than 50 percent of the cannabinoid of the composition by mass; the solid phase comprises a crystal phase that consists of one or more crystals; the crystal phase comprises at least 90 percent of the cannabinoid of the solid phase by mass; the crystal phase comprises the cannabinoid at a concentration of at least 90 percent by mass; the composition comprises the liquid phase and the crystal phase at a ratio of at least 1:10 and no greater than 20:1 by mass; and the composition lacks molecules that comprise at least 5 carbon atoms and no greater than 16 carbon atoms at a concentration greater than 20 percent by mass.

Various aspects of this patent document relate to a composition, comprising a cannabinoid, an impurity, a liquid phase, and a solid phase, wherein: either the cannabinoid is cannabidiol and the impurity is tetrahydrocannabinol or the cannabinoid is cannabidivarin and the impurity is tetrahydrocannabivarin; the composition comprises the cannabinoid and the impurity at a ratio of at least 3:1 and no greater than 333:1 by mass; the liquid phase consists of one or more liquids; the liquid phase has an average density of at least 770 and no greater than 1260 grams per liter; the liquid phase comprises greater than 50 percent of the impurity of the composition by mass; the solid phase consists of one or more solids; the solid phase comprises greater than 50 percent of the cannabinoid of the composition by mass; the solid phase comprises a crystal phase that consists of one or more crystals; the crystal phase comprises at least 90 percent of the cannabinoid of the solid phase by mass; the crystal phase comprises the cannabinoid at a concentration of at least 90 percent by mass; the composition comprises the liquid phase and the crystal phase at a ratio of at least 1:10 and no greater than 20:1 by mass; and the composition lacks molecules that comprise at least 5 carbon atoms and no greater than 16 carbon atoms at a concentration greater than 20 percent by mass.

In some specific embodiments, the composition lacks molecules that comprise at least 5 carbon atoms and no greater than 16 carbon atoms at a concentration greater than 10 percent by mass. In some very specific embodiments, the composition lacks molecules that comprise at least 5 carbon atoms and no greater than 16 carbon atoms at a concentration greater than 5 percent by mass.

In some embodiments, the composition lacks n-propane; n-butane; n-pentane; n-hexane; n-heptane; n-octane; n-nonane; n-decane; n-undecane; n-dodecane; n-tridecane; n-tetradecane; n-pentadecane; n-hexadecane; 3,6-dimethyltridecane; 2,6-dimethyl-tetradecane; beta-caryophyllene; humulene; limonene; myrcene; ocimene; pinene; terpinolene; bisabolol; eucalyptol; guaiol; nerolidol; and linalool at a combined concentration greater than 20 percent by mass such as 10, 5, or 1 percent by mass.

In some embodiments, the one or more liquids of the liquid phase comprises a water-miscible liquid that is miscible with water; and the water-miscible liquid comprises water. In some specific embodiments, the water-miscible liquid comprises water at a concentration of at least 30 molar and less than 55.5 molar.

In some embodiments, the water-miscible liquid comprises an alcohol at a concentration of at least 10 parts per million and no greater than 50 percent by mass. In some specific embodiments, the alcohol is isopropanol. In some specific embodiments, the alcohol is ethanol.

In some embodiments, the water-miscible liquid comprises glycerol.

In some embodiments, the water-miscible liquid comprises a metal cation, and the metal cation is dissolved in the water-miscible liquid. In some specific embodiments, the metal cation is sodium cation. In some specific embodiments, the metal cation is potassium cation. In some specific embodiments, the metal cation is magnesium cation. In some specific embodiments, the metal cation is calcium cation. In some very specific embodiments, the water-miscible liquid comprises the metal cation at a concentration of at least 10 milligrams per liter.

In some embodiments, the water-miscible liquid comprises an anion, and the anion is dissolved in the water-miscible liquid. In some specific embodiments, the anion is chloride. In some specific embodiments, the anion is fluoride. In some specific embodiments, the anion is bicarbonate. In some specific embodiments, the anion is sulfate. In some specific embodiments, the anion is dihydrogen phosphate. In some very specific embodiments, the water-miscible liquid comprises the anion at a concentration of at least 10 micrograms per liter.

In some embodiments, the liquid phase comprises the water-miscible liquid at a concentration of at least 20 percent by mass.

In some embodiments, the one or more liquids of the liquid phase comprise a water-immiscible liquid that is not miscible with water.

In some embodiments, the water-immiscible liquid comprises at least 50 percent of the impurity of the composition by mass.

In some embodiments, the one or more liquids of the liquid phase comprises a water-miscible liquid that is miscible with water and a water-immiscible liquid that is not miscible with water; the water-miscible liquid has a density; the water-immiscible liquid has a density; and the absolute value of the difference between the density of the water-miscible liquid and the density of the water-immiscible liquid is no greater than 200 grams per liter.

In some embodiments, the one or more crystals are thermodynamically stable relative to dissolution into the liquid phase.

In some embodiments, the solid phase is suspended in the liquid phase.

In some embodiments, the cannabinoid is 2-[(1R,6R)-6-isopropenyl-3-methylcyclohex-2-en-1-yl]-5-alkylbenzene-1,3-diol.

In some embodiments, the cannabinoid is 2-[(2E)-3,7-dimethylocta-2,6-diene-1-yl]-5-alkylbenzene-1,3-diol.

In some embodiments, the impurity is either (2R)-2-methyl-2-(4-methylpent-3-en-1-yl)-5-hydroxy-7-alkyl-2H-1-benzopyran or (2S)-2-methyl-2-(4-methylpent-3-en-1-yl)-5-hydroxy-7-alkyl-2H-1-benzopyran.

In some embodiments, the impurity is (6aR,10aR)-6,6,9-trimethyl-3-alkyl-6a,7,8,10a-tetrahydro-6H-benzo[c]chromen-1-ol.

In some embodiments, the impurity is (6aS,10aR)-6,6,9-trimethyl-3-alkyl-6a,7,8,10a-tetrahydro-6H-benzo[c]chromen-1-ol.

In some embodiments, the impurity is 6,6,9-trimethyl-3-alkyl-6H-benzo[c]chromen-1-ol.

In some embodiments, alkyl is propyl or pentyl.

Various aspects of this patent document relate to a method to purify a cannabinoid, comprising (i) providing a composition described anywhere in this patent document, and (ii) separating the solid phase of the composition and the liquid phase of the composition to purify the cannabinoid.

Various aspects of this patent document relate to a method to purify a cannabinoid, comprising (i) crystallizing a cannabinoid to produce a composition described anywhere in this patent document, and (ii) separating the solid phase of the composition and the liquid phase of the composition to purify the cannabinoid.

In some embodiments, separating is performed by one or more of: filtering the composition; centrifuging the composition; and stratifying the composition into layers and then mechanically separating a layer comprising a majority of the solid phase from a layer comprising a majority of the liquid phase.

What is claimed is:

1. A method to produce cannabinoid crystals, comprising:
   (a) providing a precursor composition that comprises (i) a precursor, (ii) contaminant precursors, (iii) original lipids, and (iv) original organic matter, wherein:
      either (i) the precursor is cannabidiolic acid, and the contaminant precursors consist of tetrahydrocannabinolic acid and cannabichromenic acid, or (ii) the precursor is cannabidivarnic acid, and the contaminant precursors consist of tetrahydrocannabivarin acid and cannabichromevarin acid;
      the original lipids consist of one or more of n-nonane; n-decane; n-undecane; n-dodecane; n-tridecane; n-tetradecane; n-pentadecane; n-hexadecane; n-heptadecane; n-octadecane; n-nonadecane; n-icosane; n-heneicosane; n-docosane; n-tricosane; n-tetracosane; n-pentacosane; n-hexacosane; n-heptacosane; n-octacosane; n-nonacosane; n-triacontane; n-hentriacontane; n-dotriacontane; 3,6-dimethyl-tridecane; 2,6-dimethyl-tetradecane; 2,6-dimethyl-hexadecane; 3,6-dimethyl-heptadecane; 3,7-dimethyl-heptadecane; 3,6-dimethyl-octadecane; 3,7-dimethyl-octadecane; 3-methyl-heneicosane; 3-methyl-tricosane; 2-methyl-tetracosane; 3-methyl-pentacosane; 2-methyl-hexacosane; 3-methyl-heptacosane; and 3-methyl-triacontane;
      the original organic matter consists of plant-derived molecules and ions that do not vaporize at any temperature of less than 235 degrees Celsius at atmospheric pressure; and
      the precursor composition comprises the precursor at a concentration of at least 4 percent by mass;
   (b) heating the precursor composition to produce a decarboxylated composition that comprises (i) a cannabinoid, (ii) contaminants, (iii) lipids, and (iv) organic matter, wherein:
      the heating converts at least 90 percent of the precursor into (i) the cannabinoid and (ii) carbon dioxide by mole of the precursor;
      either (i) the precursor is cannabidiolic acid, and the cannabinoid is cannabidiol, or (ii) the precursor is cannabidivarnic acid, and the cannabinoid is cannabidivarin;
      the heating converts at least 90 percent of the contaminant precursors into (i) the contaminants and (ii) carbon dioxide by mole of the contaminant precursors;
      either (i) the contaminant precursors consist of tetrahydrocannabinolic acid and cannabichromenic acid, and the contaminants consist of tetrahydrocannabinol and cannabichromene, or (ii) the contaminant precursors consist of tetrahydrocannabivarin acid and cannabichromevarin acid, and the contaminants consist of tetrahydrocannabivarin and cannabichromevarin;
      the lipids consist of a portion of the original lipids that survive the heating; and
      the organic matter consists of a portion of the original organic matter that survives the heating;
   (c) combining a portion of the decarboxylated composition with ethanol to produce a dewaxing composition that comprises (i) ethanol, (ii) a portion of the cannabinoid of the decarboxylated composition, (iii) a portion of the contaminants of the decarboxylated composition, (iv) a portion of the lipids of the decarboxylated composition, and (v) a portion of the organic matter of the decarboxylated composition, wherein:
      the portion of the cannabinoid of the decarboxylated composition comprises the cannabinoid at a concentration of at least 30 percent and no greater than 80 percent by mass;
      the portion of the cannabinoid of the decarboxylated composition comprises the cannabinoid and the contaminants at a ratio of at least 3:1 and no greater than 80:1 by mass;
      the portion of the cannabinoid of the decarboxylated composition comprises the cannabinoid and the lipids at a concentration of at least 1:2 and no greater than 40:1 by mass;
      the portion of the cannabinoid of the decarboxylated composition comprises the cannabinoid and the organic matter at a concentration of at least 1:2 and no greater than 40:1 by mass; and
      the dewaxing composition comprises the ethanol at a concentration of at least 20 percent and no greater than 90 percent by mass;
   (d) cooling a portion of the dewaxing composition to produce a mixture that comprises (i) a portion of the ethanol of the dewaxing composition, (ii) a portion of the cannabinoid of the dewaxing composition, (iii) a portion of the contaminants of the dewaxing composition, (iv) a portion of the lipids of the dewaxing composition, and (v) a portion of the organic matter of the dewaxing composition, wherein:
      the mixture comprises a solid phase and a liquid phase;
      the cooling converts at least 65 percent of the portion of the lipids of the dewaxing composition into solid-phase lipids by mass such that the solid phase of the mixture comprises at least 65 percent of the lipids of the mixture by mass;
      the liquid phase comprises at least 90 percent of the ethanol of the mixture by mass;
      the liquid phase comprises at least 90 percent of the cannabinoid of the mixture by mass;
      the liquid phase comprises at least 90 percent of the contaminants of the mixture by mass; and
      the liquid phase comprises at least a portion of the organic matter of the mixture;
   (e) separating a portion of the liquid phase from the solid phase to produce a dewaxed composition that comprises (i) a portion of the ethanol of the liquid phase, (ii) a portion of the cannabinoid of the liquid phase, (iii) a portion of the contaminants of the liquid phase, and (iv) a portion of the organic matter of the liquid phase;

(f) separating ethanol from a portion of the dewaxed composition to produce a concentrate composition that comprises (i) a portion of the cannabinoid of the dewaxed composition, (ii) a portion of the contaminants of the dewaxed composition, and (iii) a portion of the organic matter of the dewaxed composition, wherein:
 the separating is performed by vaporizing the ethanol from the portion of the dewaxed composition; and
 the concentrate composition lacks ethanol at a concentration greater than 20 percent by mass;

(g) heating a portion of the concentrate composition to produce a vapor phase and residual organic matter, wherein:
 the portion of the concentrate composition comprises the cannabinoid and the contaminants at a combined concentration of at least 40 percent and no greater than 85 percent by mass;
 the vapor phase comprises (i) a portion of the cannabinoid of the concentrate composition and (ii) a portion of the contaminants of the concentrate composition;
 the residual organic matter comprises a portion of the organic matter of the concentrate composition; and
 the residual organic matter consists of one or both of a solid and a liquid;

(h) separating a portion of the vapor phase from the residual organic matter to produce a distillate that comprises (i) a portion of the cannabinoid of the vapor phase, and (ii) a portion of the contaminants of the vapor phase;

(i) condensing a portion of the distillate into a condensed phase that comprises (i) a portion of the cannabinoid of the distillate, and (ii) a portion of the contaminants of the distillate, wherein:
 the condensed phase comprises the cannabinoid at a concentration of at least 70 percent and no greater than 90 percent by mass; and
 the condensed phase comprises the contaminants at a concentration of at least 1 percent and no greater than 20 percent by mass;

(j) combining a portion of the condensed composition and ethanol to produce a crystallization composition that comprises (i) ethanol, (ii) a portion of the cannabinoid of the condensed phase, and (iii) a portion of the contaminants of the condensed phase;

(k) incubating a portion of the crystallization composition at a crystallization temperature to produce crystals and residual liquid, wherein:
 the cannabinoid has both a concentration and a solubility in the portion of the crystallization composition, and the crystallization temperature is a temperature at which the concentration is greater than the solubility;
 the crystals comprise a portion of the cannabinoid of the crystallization composition; and
 the residual liquid comprises a portion of the ethanol of the crystallization composition and a portion of the contaminants of the crystallization composition; and (l) separating a portion of the crystals from the residual liquid to produce a product, wherein:
 the product comprises the cannabinoid at a concentration of at least 90 percent by mass;
 the product lacks the contaminants at a concentration of greater than 0.3 percent by mass;
 the product lacks the lipids at a concentration of greater than 1 percent by mass;
 the product lacks the organic matter at a concentration greater than 1 percent by mass;
 the crystals are a solid;
 the crystals have a melting point; and
 the crystals lack a glass-transition temperature.

2. A composition, comprising a cannabinoid, an impurity, a liquid phase, and a solid phase, wherein:
 the cannabinoid has the molecular formula $C_xH_yO_2$;
 the impurity has the molecular formula $C_xH_zO_2$;
 "x" is at least 17 and no greater than 24;
 "y" is at least 22 and no greater than 36;
 "z" is at least 22 and no greater than 34;
 the cannabinoid and the impurity each comprise an alkyl;
 the alkyl of the cannabinoid is identical to the alkyl of the impurity;
 the alkyl is either methyl, propyl, pentyl, or heptyl;
 the cannabinoid is either (i) 2-[(1R,6R)-6-isopropenyl-3-methylcyclohex-2-en-1-yl]-5-alkylbenzene-1,3-diol, and "z" equals "y" minus either 0, 2, or 4, or (ii) 2-[(2E)-3,7-dimethylocta-2,6-diene-1-yl]-5-alkylbenzene-1,3-diol, and "z" equals "y" minus either 2, 4, or 6;
 the impurity comprises a 2H-chromene ring that either (i) comprises exactly 4 substituents that consist of a 2-methyl substituent; a 2-(4-methylpent-3-en-1-yl) substituent; a 5-hydroxy substituent; and a 7-alkyl substituent that is the alkyl of the impurity, wherein "z" equals "y" minus either 0 or 2 or (ii) is the 2H-chromene of a 6H-benzo[c]chromene ring that comprises exactly 5 substituents that consist of a 1-hydroxy substituent; a 3-alkyl substituent that is the alkyl of the impurity; two 6-methyl substituents; and a 9-methyl substituent, wherein "z" equals "y" minus either 0, 2, 4, or 6;
 the composition comprises the cannabinoid and the impurity at a ratio of at least 3:1 and no greater than 333:1 by mass;
 the liquid phase consists of one or more liquids;
 the liquid phase has an average density of at least 770 and no greater than 1260 grams per liter;
 the liquid phase comprises greater than 50 percent of the impurity of the composition by mass;
 the liquid phase is in both physical and chemical communication with the solid phase such that the physical and chemical properties of the composition control the extent to which the cannabinoid partitions between the liquid phase and the solid phase;
 the solid phase consists of one or more solids;
 the solid phase comprises greater than 50 percent of the cannabinoid of the composition by mass;
 the solid phase comprises a crystal phase that consists of one or more crystals;
 the crystal phase comprises at least 90 percent of the cannabinoid of the solid phase by mass;
 the crystal phase comprises the cannabinoid at a concentration of at least 90 percent by mass;
 the composition comprises the liquid phase and the crystal phase at a ratio of at least 1:10 and no greater than 20:1 by mass; and
 the composition lacks molecules that comprise at least 5 carbon atoms and no greater than 16 carbon atoms at a concentration greater than 20 percent by mass.

3. A composition, comprising a cannabinoid, an impurity, a liquid phase, and a solid phase, wherein:
- either the cannabinoid is cannabidiol and the impurity is tetrahydrocannabinol or the cannabinoid is cannabidivarin and the impurity is tetrahydrocannabivarin;
- the composition comprises the cannabinoid and the impurity at a ratio of at least 3:1 and no greater than 333:1 by mass;
- the liquid phase consists of one or more liquids;
- the liquid phase has an average density of at least 770 and no greater than 1260 grams per liter;
- the liquid phase comprises greater than 50 percent of the impurity of the composition by mass;
- the solid phase consists of one or more solids;
- the solid phase comprises greater than 50 percent of the cannabinoid of the composition by mass;
- the solid phase comprises a crystal phase that consists of one or more crystals;
- the crystal phase comprises at least 90 percent of the cannabinoid of the solid phase by mass;
- the crystal phase comprises the cannabinoid at a concentration of at least 90 percent by mass;
- the composition comprises the liquid phase and the crystal phase at a ratio of at least 1:10 and no greater than 20:1 by mass; and
- the composition lacks molecules that comprise at least 5 carbon atoms and no greater than 16 carbon atoms at a concentration greater than 20 percent by mass.

4. The composition of claim 3, wherein the composition lacks n-propane; n-butane; n-pentane; n-hexane; n-heptane; n-octane; n-nonane; n-decane; n-undecane; n-dodecane; n-tridecane; n-tetradecane; n-pentadecane; n-hexadecane; 3,6-dimethyl-tridecane; 2,6-dimethyl-tetradecane; beta-caryophyllene; humulene; limonene; myrcene; ocimene; pinene; terpinolene; bisabolol; eucalyptol; guaiol; nerolidol; and linalool at a combined concentration greater than 20 percent by mass.

5. The composition of claim 3, wherein the one or more liquids of the liquid phase comprises a water-miscible liquid that is miscible with water; and the water-miscible liquid comprises water.

6. The composition of claim 5, wherein the water-miscible liquid comprises water at a concentration of at least 30 molar and less than 55.5 molar.

7. The composition of claim 5, wherein the water-miscible liquid comprises an alcohol at a concentration of at least 10 parts per million and no greater than 50 percent by mass.

8. The composition of claim 7, wherein the alcohol is isopropanol.

9. The composition of claim 7, wherein the alcohol is ethanol.

10. The composition of claim 5, wherein the water-miscible liquid comprises glycerol.

11. The composition of claim 5, wherein the water-miscible liquid comprises an anion, the anion is bicarbonate, and the bicarbonate is dissolved in the water-miscible liquid.

12. The composition of claim 5, wherein the liquid phase comprises the water-miscible liquid at a concentration of at least 20 percent by mass.

13. The composition of claim 3, wherein the one or more liquids of the liquid phase comprise a water-immiscible liquid that is not miscible with water.

14. The composition of claim 13, wherein the water-immiscible liquid comprises at least 50 percent of the impurity of the composition by mass.

15. The composition of claim 3, wherein:
- the one or more liquids of the liquid phase comprises a water-miscible liquid that is miscible with water and a water-immiscible liquid that is not miscible with water;
- the water-miscible liquid has a density;
- the water-immiscible liquid has a density; and
- the absolute value of the difference between the density of the water-miscible liquid and the density of the water-immiscible liquid is no greater than 200 grams per liter.

16. The composition of claim 3, wherein the one or more crystals are thermodynamically stable relative to dissolution into the liquid phase.

17. The composition of claim 3, wherein the solid phase is suspended in the liquid phase.

18. A method to purify a cannabinoid, comprising (i) providing a composition according to claim 3, and (ii) separating the solid phase of the composition and the liquid phase of the composition to purify the cannabinoid.

19. A method to purify a cannabinoid, comprising (i) crystallizing a cannabinoid to produce a composition according to claim 3, and (ii) separating the solid phase of the composition and the liquid phase of the composition to purify the cannabinoid.

20. The method of claim 18, wherein the separating is performed by one or more of:
- filtering the composition;
- centrifuging the composition; and
- stratifying the composition into layers and then mechanically separating a layer comprising a majority of the solid phase from a layer comprising a majority of the liquid phase.

* * * * *